United States Patent [19]

Deutsch et al.

[11] Patent Number: 5,190,742

[45] Date of Patent: Mar. 2, 1993

[54] DEVICE AND METHOD FOR CARRYING OUT A PLURALITY OF SEQUENTIAL TRANSFORMATIONS OF A SUBSTRATE

[75] Inventors: Edward Deutsch; Karen Libson, both of St. Louis, Mo.; Fabio Lunghi, Turin, Italy

[73] Assignee: Sorin Biomedica S.p.A., Italy

[21] Appl. No.: 543,695

[22] Filed: Jun. 26, 1990

[30] Foreign Application Priority Data

Jun. 28, 1989 [IT]  Italy .................................. 67529 A/89

[51] Int. Cl.$^5$ ..................... A61K 43/00; B01J 19/90; B01J 69/00
[52] U.S. Cl. ................................... 424/1.1; 422/130; 422/149; 206/223; 206/438; 206/569; 206/571
[58] Field of Search ..................... 424/1.1; 428/402.2, 428/402.24; 422/130, 149, 159, 239; 206/223, 569, 438, 571

[56] References Cited

U.S. PATENT DOCUMENTS

| | | | |
|---|---|---|---|
| 3,042,622 | 7/1962 | Kirschenbauer | 252/183.13 X |
| 4,471,055 | 9/1984 | Opp | 436/128 |
| 4,775,638 | 10/1988 | Haisma | 424/1.1 X |

Primary Examiner—Robert L. Stoll
Assistant Examiner—John M. Covert
Attorney, Agent, or Firm—Wood, Herron & Evans

[57] ABSTRACT

A device or kit having inlet means for introducing within the kit a first reagent, includes a substrate and at least a second reagent in the form of microcapsules adapted to release, according to a predetermined release profile, the second reagent after the first reagent has been introduced into the kit. The device allows to carry out at least two and optionally more transformations of the physical and/or chemical properties of the substrate by means of a single step procedure by the operator consisting of the introduction of the first reagent.

The invention particularly relates to the preparation of stable injectable preparations of radiopharmaceuticals.

11 Claims, No Drawings

DEVICE AND METHOD FOR CARRYING OUT A PLURALITY OF SEQUENTIAL TRANSFORMATIONS OF A SUBSTRATE

The present invention relates to a device and method for carrying out a plurality of sequential transformations of the chemical or physical properties of a given substrate by means of a single step procedure.

More particularly the invention relates to a device and method for conducting sequential chemical reactions between a substrate and two or more reactants which, in order to provide the desired end product, must be put sequentially into contact with the substrate.

The term "transformation" as used herein is intended to mean any modification of the chemical nature of a substrate or of its physical properties.

In the field of the therapeutic and diagnostic pharmaceuticals, use is made of sealed kits which contain under sterile conditions a substrate constituting a first chemical reactant. Such kits are provided with inlet means consisting of a resilient stopper adapted to be punctured by a hypodermic needle for injecting within the kit a second reactant which reacts with the substrate contained therein in order to provide a sterile injectable formulation suitable for administration e.g. to a human body. In some cases it is desired, after injection of the second reactant to deliver into contact with the reaction product a further reactant; this however requires a second injection within the kit which in some cases is troublesome and may be the cause of human error. It is in fact clear that the more complex and the higher the number of steps requiring intervention by the operator, the higher the possibility of human error and risk of contamination.

Thus a first object of the present invention is to provide a device and method which would minimize the chances for error by minimizing the number of steps a technician has to perform in order to obtain the desired end product.

More particularly the present invention has been developed in connection with the preparation of 99m-Tc radiopharmaceuticals which are very important agents in the diagnosis of a variety of disease states, including brain disorders such as stroke, Alzheimer's disease etc.

These agents are prepared from 99m-pertechnetate which is obtained from a 99-Mo/99m-Tc generator. The 99m-pertechnetate must be reduced in the presence of a ligand in order to prepare useful 99m-Tc radiopharmaceuticals. This chemical transformation (reduction plus chelation) is accomplished in an "instant kit" by injecting a saline solution of 99m-pertechnetate (from the 99-Mo/99m-Tc generator) into the kit. The kit contains a lyophilized, sterile solid which most often consists of a reductant and a chelating ligand, but can also contain a stabilizer (such as ascorbic acid or gentisic acid which function as anti-oxidants to prevent the reduced 99m-Tc agent from being reoxidized to 99m-pertechnetate). The reductant most often used is stannous ion such as contained in stannous chloride and stannous tartrate.

With current technology, all instant kit formulations are capable of performing only one chemical step; the kit can be heated to make this step proceed faster, but there is no convenient way to perform two distinct chemical steps within a single kit. A second step can be performed by having a second kit. After the first kit is formulated, the second kit can be reconstituted and its contents then injected into the first kit. This is a "two stick" approach to the problem, and it leads to difficulties in clinical practice since, as mentioned above, the more steps that a technician has to perform, the more chance there is for error such as injection of kits in the wrong order, lack of sterility, and subsequent harm to the patient due to injection of an inappropriate or even dangerous radiochemical formulation.

Thus a further more specific object of the present invention is to provide a device and method allowing the preparation of radiopharmaceutical formulations by means of a single step approach.

Further objects of the present invention will be apparent from the description which follows and will readily appear to those skilled in the art.

As a result of the invention, we have shown that at least two, but in principle several chemical or physical steps can be performed in a single kit by the use of microcapsules. Thus, the invention provides a device for carrying out a plurality of sequential transformations of the chemical or physical properties of a substrate by means of a single step procedure comprising:

a volume provided with inlet means for introducing within said volume a first substance adapted to contact said substrate in order to cause a first transformation thereof, and within said volume, a given amount of said substrate and a given amount of at least a second substance, said second substance being in the form of microcapsules adapted to release said second substance with a given release profile after having been contacted by said first substance in order to cause a second transformation.

According to the invention a substance, such as a chemical reagent, is encapsulated within protective coatings which dissolve and release the encapsulated reagents at a known rate or at a known time. Thus, after the initial reaction, a second reagent can be released at a subsequent time to perform a second reaction; in principle, several reactions can be performed in sequence with a single kit by timed release of various reagents contained in microcapsules having different release properties.

The term "microcapsules" as used herein, is intended to mean both reservoir microcapsules which have a central core of a substance coated with a polymeric membrane and monolithic microcapsules, sometimes known as microspheres, wherein the substance to be released is homogeneously dispersed throughout a polymeric matrix.

It is known that microcapsules may be designed in order to provide for the desired release profile depending on the environment of use and encapsulated substance, by appropriate selection of the polymeric matrix or coating.

The microcapsules used according to the invention may thus provide for a sharp release, a delayed or sustained release and a constant release, depending upon the specific application.

Microcapsules for use according to the invention may be prepared by known methods, such as disclosed in U.S. Pat. No. 3,773,919. Additionally microcapsules may be prepared by the in-water-dry method disclosed in EP-A-0 145 240.

It is understood that for all those applications of the invention wherein the end product resulting from the sequential transformations has to be administered to a human or animal body, the material constituting the microcapsule coating or matrix must be injectable and the microcapsule must be sterile and pyrogen free.

U.S. Pat. No. 3,773,919 and EP-A-058481 disclose polylactide polymers which are biocompatible and provide for the release of various drugs at a constant release rate.

Further biocompatible microcapsules include those wherein the coating consists of albumin or polyethylene glycol based surfactants.

Additional information on microcapsules are given in the list of references provided at the end of the present specification.

The invention also relates to a method for carrying out a plurality of sequential transformations of the physical or chemical properties of a substrate by means of a single step procedure, comprising:

providing a volume having inlet means for introducing within said volume a first substance adapted to contact said substrate in order to cause a first transformation thereof, said volume including a given amount of said substrate and a given amount of at least a second substance encapsulated in the form of microcapsules adapted to release said second substance with a given release profile after having been contacted by said first substance in order to cause a second transformation, and introducing within said volume a given amount of said first substance.

The invention will be further described by means of the following example.

EXAMPLE 1

The Example specifically relates to the preparation of the radiopharmaceuticals 99m-Tc HM-PAO and 99m-Tc CB-PAO.

To obtain acceptable yields of these agents from 99m-pertechnetate, the synthetic reaction (reduction by stannous ion in the presence of the ligand, either HM-PAO or CB-PAO) must be carried out at a relatively high pH value of about 9. However, the subsequently formed 99m-Tc radiopharmaceutical is relatively unstable at this high pH and thus must be used, i.e. injected into the patient, within 30 minutes of its formulation. After 30 minutes, too much decomposition has occurred to make this agent useful. Also, before injection, the agent must be subjected to strict quality control procedures which require about 15 minutes. Thus, the agent is only usable in the clinic for a 15 minute period, from about 15 minutes after formulation to about 30 minutes after formulation.

However these agents are much more stable at lower pH values of about 7. They cannot be formed at this pH, but if they could be brought to this pH after formulation, then the stability would be greatly enhanced. This approach was demonstrated by Hung et al. in JNM 29: 935, 1988. This is the "two step" approach.

According to the invention it has been shown that by incorporating an acid, namely gentisic acid plus phosphate buffer, into microspheres, the initial reduction can be conducted at a pH about 9, and then within a single kit the microspheres subsequently release the gentisic acid and phosphate buffer to bring the pH down to about 7 and the final formulation has greater than 6 hours stability. Thus this invention allows two successive reactions to occur in a single "instant kit", and allows the conversion of an agent which is difficult to use in the clinic into one which is readily used and is very convenient.

Two samples of Na gentisate microspheres/microcapsules were prepared.

Data for the samples is as follows:

| Sample No. | 8-511 A | 8-512 |
| --- | --- | --- |
| Shell: | Polyethylene Glycol E 4500NF (Dow) | Polyethylene Glycol E 4500NF (Dow) |
| Fill: | Na gentisate Na$_2$HPO$_4$ | 8-511A microspheres |
| Size: | A: 425–710 μm | 425–710 μm |
| Theoretical payload: | 15% (fill by wt.) | 80% microspheres by wt. or 12% salt mixture |
| Method: | Rotating disk | Air suspension coated |
| Collection: | Purity Gum 59 | None |
| Sample wt.: | A = 60 g; | 10 g |

The sodium gentisate and disodium phosphate were mixed in a ratio of 1:2.9 and dissolved in water. The pH was adjusted to 7.2 with dilute HCl and the mixture was freeze dried.

The dried salt was milled to reduce the particle size for encapsulation. The microspheres (sample 8-511A) were prepared by using a rotating disk and collected in Purity Gum 59 (cold water soluble starch). Microspheres from 8-511A were overcoated (sample 8-512) using an air suspension coater.

10 mg of microspheres of sample 8-512 were charged into a standard kit including the conventional amount of CB-PAO. The use of 10 mg of microspheres in this standard kit allowed the original reaction to be conducted at a pH 8.74 and then within one minute the pH was lowered to pH 7.36. The final formulation was of 97% purity and was stable for at least 3 hours.

It is understood that the present invention is not limited to the specific example provided herein. Other possible applications include the following:

Formulation of 186-Re(Sn)-HEDP

186-Re(Sn)-HEDP is an agent in development for palliation of pain associated with metastatic cancer to bone. This agent must be formulated at an acidic pH of about 2, but cannot be injected at this pH value. Raising the pH now demands a second kit and a second "stick". The same microsphere approach described above could be used to raise the pH after formulation within a single kit.

Production of 99 m-Tc Radiopharmaceuticals

U.S. Pat. No. 4,795,626 relates to "non-reducible" Tc(III) cations for heart imaging and describes the production of 99 m-Tc radiopharmaceuticals by two successive chemical steps: initial reduction of 99 m-pertechnetate to a Tc(V) intermediate and then subsequent conversion to a Tc(III) product. This now requires two separate kits. However, the microsphere approach according to the invention would allow these two chemical steps to be conducted in a single kit; the reagent used to convert Tc(V) to Tc(III) may be incorporated into microcapsules and then released into the reaction mixture only after the initial formation of Tc(V) was completed.

LIST OF REFERENCES

Kim, C.K. et al., "Development of Hydrophilic Human Serum Albumin Microspheres Using a Drug-Albumin Conjugate" in Int. J. Pharm., 47 (1–3), 163–9.

Tomlinson, E. et al., "Human Serum Albumin Microspheres for Intra-arterial Drug Targeting of Cytostatic Compounds" in Microspheres Drug Ter.: Pharm., Immunol., Med. Aspects, Meeting date 1983, 75-89 edited by Davis, Stanleys Elsevier.

U.S. Pat. No. 4,622,244.

Tice, T.R. et al., "Preparation of Injectable Controlled-Release Microcapsules by a Solvent-Evaporation Process" in J. Controlled Release, 2, 343-52.

European Patent Application EP 257,368.

We claim:

1. A device for carrying out a plurality of sequential transformations of a pharmaceutical by means of a single step procedure comprising:

a volume containing a substrate, said volume provided with inlet means for introducing within said volume a first substance adapted to contact said substrate in order to cause a first transformation thereof, and within said volume a given amount of at least a second substance, said second substance encapsulated in sterile pyrogen free biocompatible microcapsules adapted to release said second substance with a given release profile after having been contacted by said first substance in order to cause a second transformation to thereby form an injectable pharmaceutical.

2. A device according to claim 1, wherein said volume is a kit provided with resilient stopper means adapted to be punctured for injection of said first substance.

3. The device claimed in claim 1 wherein said pharmaceutical is a radiopharmaceutical and said first substance comprising a radioactive composition.

4. The device claimed in claim 3 wherein said radioactive composition is selected from the group consisting of rhenium compositions and technetium compositions.

5. A device according to claim 1 for preparing by a two step transformation a stable injectable 99 m-Tc radiopharmaceutical, wherein said volume consists of a kit, said substrate comprises a reductant and/or a chelating agent, said microcapsules include a pH controlling agent, and said first substance comprises 99 m-pertechnetate.

6. A device according to claim 5, wherein the second substance is gentisic acid and a buffer.

7. A device according to claim 6, wherein said microcapsules have a poly-ethylene glycol shell.

8. A method for carrying out a plurality of sequential transformations of the physical or chemical properties of a substrate by means of a single step procedure to form an injected pharmaceutical comprising:

providing a volume having inlet means for introducing within said volume a first substance adapted to contact said substrate in order to cause a first transformation thereof, said volume including a given amount of substrate and a given amount of at least a second substance encapsulated in the form of sterile, pyrogen free biocompatible microcapsules adapted to release said second substance with a given release profile after having been contacted by said first substance in order to cause a second transformation, and introducing within said volume a given amount of said first substance to thereby form an injectable pharmaceutical.

9. The method claimed in claim 8 wherein said injectable pharmaceutical is a radiopharmaceutical and said first substance is a radioactive composition.

10. The method claimed in claim 9 wherein said radioactive composition is selected from the group consisting of technetium compositions and rhenium compositions.

11. A method according to claim 8 for preparing a stable injectable formulation of 99 m-Tc radiopharmaceuticals wherein said volume consists of a kit including as a substrate a reductant and/or a chelating agent, said microcapsules include a pH controlling agent, the method comprising injecting within said kit an amount of 99 m-pertechnetate.

* * * * *